United States Patent [19]

Pallenberg et al.

[11] Patent Number: 5,538,945
[45] Date of Patent: Jul. 23, 1996

[54] STIMULATION OF HAIR GROWTH BY PEPTIDE COPPER COMPLEXES

[75] Inventors: Alexander J. Pallenberg, Duval; Leonard M. Patt, Seattle; Ronald E. Trachy, Bothell, all of Wash.

[73] Assignee: ProCyte Corporation, Kirkland, Wash.

[21] Appl. No.: 261,475

[22] Filed: Jun. 17, 1994

[51] Int. Cl.$^6$ .................................................. A61K 38/04
[52] U.S. Cl. .................................. 514/6; 514/18; 514/19; 530/304
[58] Field of Search ............................ 514/6, 18, 19; 530/304

[56] References Cited

U.S. PATENT DOCUMENTS

| | | | |
|---|---|---|---|
| 3,194,732 | 7/1965 | Neuhauser | 167/58 |
| 3,551,554 | 12/1970 | Herschler | 424/7 |
| 3,558,770 | 1/1971 | Gordon et al. | 424/80 |
| 3,758,682 | 9/1973 | Huber et al. | 424/177 |
| 3,767,784 | 10/1973 | Gluck | 424/28 |
| 3,832,338 | 8/1974 | Huber et al. | 260/113 |
| 4,022,888 | 5/1977 | Huber et al. | 424/177 |
| 4,167,945 | 9/1979 | Gottlieb | 128/334 R |
| 4,177,261 | 12/1979 | Dietze et al. | 424/101 |
| 4,263,428 | 4/1981 | Apple et al. | 536/17 A |
| 4,287,184 | 9/1981 | Young | 424/177 |
| 4,440,788 | 4/1984 | Terayama et al. | 424/320 |
| 4,665,054 | 5/1987 | Pickart | 514/18 |
| 4,760,051 | 7/1988 | Pickart | 514/6 |
| 4,767,753 | 8/1988 | Pickart | 514/18 |
| 5,120,831 | 6/1992 | Pickart | 530/331 |
| 5,177,061 | 1/1993 | Pickart | 514/18 |
| 5,214,032 | 5/1993 | Pickart | 514/16 |
| 5,252,559 | 10/1993 | Kronholm et al. | 514/18 |
| 5,470,876 | 11/1995 | Proctor | 514/492 |

FOREIGN PATENT DOCUMENTS

| | | |
|---|---|---|
| 327263A1 | 8/1989 | European Pat. Off. . |
| WO87/00427 | 1/1987 | WIPO . |
| WO88/05653 | 8/1988 | WIPO . |

OTHER PUBLICATIONS

Uno, H. et al. Macaque and Rodent Models for the Screening of Drugs for Stimulating Hair Growth. Journal of Cutaneous Aging and Cosmetic Dermatology 1, 193–204 (1990).

Metzler, D. "Biochemistry", Academic Press, NY (1977). See p. 198 Table 4–2.

*Primary Examiner*—Christine M. Nucker
*Assistant Examiner*—Benet Prickril
*Attorney, Agent, or Firm*—Seed and Berry

[57] ABSTRACT

Peptide-copper complexes are disclosed which stimulate the growth of hair on warm-blooded animals. In one aspect of this invention, the peptide-copper complexes are dipeptides or tripeptides chelated to copper at a molar ratio ranging from about 1:1 to 3:1, with the second position of the peptide from the amino terminus being histidine, arginine or a derivative thereof. The peptide-copper complexes may be formulated for administration by, for example, topical application or injection. Any affliction associate with hair loss, including hair loss associated with both androgenetic and secondary alopecia, may be treated with the peptide-copper complexes of this invention.

12 Claims, No Drawings

STIMULATION OF HAIR GROWTH BY PEPTIDE COPPER COMPLEXES

TECHNICAL FIELD

This invention relates generally to peptide-copper complexes and, more specifically, to compositions containing peptide-copper complexes for stimulating hair growth.

BACKGROUND OF THE INVENTION

Hair loss is a prevalent affliction of many humans, the most common being androgenetic alopecia (AGA) where males lose scalp hair as they get older (i.e., male pattern baldness). Other hair loss afflictions include alopecia arcata (AA), female pattern baldness and hair loss secondary to chemotherapy and/or radiation treatment (i.e., secondary alopecia).

Hair is normally divided into two types: "terminal" and "veilus". Terminal hair is coarse, pigmented hair which arises from follicles which are developed deep within the dermis. Vellus hairs are typically thin,-non-pigmented hairs which grow from hair follicles which are smaller and located superficially in the dermis. As alopecia progresses, there is a change from terminal to vellus type hair. Other changes that contribute to alopecia are alterations in the growth cycle of hair. Hair typically progresses through three cycles, anagen (active hair growth), catagen (transition phase), and telogen (resting phase during which the hair shaft is shed prior to new growth). As baldness progresses, there is a shift in the percentages of hair follicles in each phase with the majority shifting from anagen to telogen. The size of hair follicles is also known to decrease while the total number remains relatively constant.

A variety of procedures and drugs have been utilized in an attempt to treat hair loss. A common technique involves hair transplantation. Briefly, plugs of skin containing hair are transplanted from areas of the scalp where hair was growing to bald or balding areas of the scalp. This procedure, however, is time-consuming and relatively painful. Other approaches include ultra-violet radiation and exercise therapy.

More recently, the stimulating hair growth has been achieved, although with limited success, by drug therapy. One of the most well-recognized hair-growth agents is sold under the tradename "Minoxidil", as disclosed in U.S. Pat. No. 4,596,812 assigned to Upjohn. However, while the results generated through the use of Minoxidil have appeared promising, there is still a need in the art for improved compositions capable of stimulating the growth of hair in warm-blooded animals. To this end, certain peptide-copper complexes have been found to be effective hair-growth agents. For example, U.S. Pat. Nos. 5,177,061, 5,120,83 1 and 5,214,032 disclose certain peptide-copper complexes which are effective in stimulating the growth of hair in warm-blooded animals.

While significant progress has been made in the stimulation of hair-growth by drug treatment, there is still a need in the art for compounds which have greater stimulatory effect on hair growth. The present invention fulfills this need, while further providing other related advantages.

SUMMARY OF THE INVENTION

Briefly stated, the present invention is directed to peptide-copper complexes, and compositions containing the same, for stimulating the growth of hair in warm-blooded animals. Compositions of this invention include one or more peptide-copper complexes in combination with an acceptable carder or diluent. As used herein, the term "copper" is used to designate copper(II) (i.e., $Cu^{+2}$).

The peptide-copper complexes of this invention are administered to an animal in need thereof in a manner which results in the application of an effective amount of the peptide-copper complex. As used herein, the term "effective amount" means an amount of the peptide-copper complex which stimulates hair growth associated with a hair-loss affiliations (such as male pattern baldness) or caused by a hair-loss insult (such as radiation or chemotherapy). Thus, the peptide-copper complexes may be used propylactically, as well as therapeutically and cosmetically. Administration of the peptide-copper complexes is preferably by topical application, although other avenues of administration may be employed, such as injection (e.g., intramuscular, intravenous, subcutaneous and intradermal). Typically, the peptide-copper complexes of this invention are formulated as a solution, cream or gel for topical application, or as a solution for injection, and include one or more acceptable carders or diluents.

As used herein, the term "peptide-copper complex" means a peptide having at least two amino acids (or amino acid derivatives) chelated to copper, wherein the second amino acid from the amino terminus of the peptide is histidine, arginine or a derivative thereof. Such peptide-copper complexes have the following general structure A:

A: $[R_1-R_2]$:copper(II)

wherein:

$R_1$ is an amino acid or an amino acid derivative; and $R_2$ is histidine, arginine or a derivative thereof.

The peptide-copper complexes of this invention have a ratio of peptide to copper ranging from about 1:1 to about 3:1, and more preferably from about 1:1 to about 2:1. In short, a component of the peptide occupies at least one coordination site of the copper ion, and multiple peptides may be chelated to a single copper ion.

In a preferred embodiment, the peptide-copper complex comprises a further chemical moiety linked to the $R_2$ moiety of structure A by an amide or peptide bond. (i.e., —C(=O)NH—). In this embodiment, the peptide-copper complex has the following structure B:

B: $[R_1-R_2-R_3]$:copper(II)

wherein:

$R_1$ is an amino acid or amino acid derivative;

$R_2$ is histidine, arginine or a derivative thereof, and $R_3$ is a chemical moiety joined to $R_2$ by an amide bond.

In a further preferred embodiment, $R_3$ of structure B is at least one amino acid joined to $R_2$ by a peptide bond. In this embodiment, the peptide-copper complex has the following structure C:

C: $[R_1-R_2-R_3]$:copper(II)

wherein:

$R_1$ is an amino acid or amino acid derivative;

$R_2$ is histidine, arginine or a derivative thereof; and $R_3$ is an amino acid or amino acid derivative joined to $R_2$ by a peptide bond, with the proviso that $R_1$ is not glycyl, alanyl, seryl or valyl when $R_2$ is histidyl or (3-methyl)histidyl and $R_3$ is lysine, lysyl-prolyl-valyl-phenylalanyl-valine, lysyl-valyl-phenylalanyl-valine, lysyl-tryptophan, or further proviso that $R_1$ is not lysyl when $R_2$ is histidyl or (3 -methyl)histidyl and $R_3$ is glycine, glycyl-prolyl-valyl-phenylalanyl-valine, glycyl-valyl-phenylalanyl-valine, glycyltryptophan, or glycyl-(glycyl)$_{1-2}$-tryptophan.

In still a further embodiment of the present invention, an additional chelating agent may be added to the peptide-copper complexes disclosed above to form a ternary peptide-copper-chelating agent complex.

Other aspects of the present invention will become evident upon reference to the following detailed description.

DETAILED DESCRIPTION OF THE INVENTION

This invention is directed to peptide-copper complexes which stimulate the growth of hair on warm-blooded animals. Such complexes are typically administered as a composition containing acceptable diluents and/or carriers. Administration is preferably by topical application directly to the area where stimulation of hair growth is desired, such as the scalp, although other routes of administration may be employed.

The peptide-copper complexes of this invention may be used to stimulate hair growth in animals (including humans) afflicted with androgenetic alopecia (AGA). Animals afflicted with this condition are usually male, and the condition results in the loss of scalp hair with age (also called "male pattern baldness"). Thus, the peptide-copper complexes may be administered in order to stimulate hair growth, thereby eliminating or reducing the severity of hair loss and/or the speed at which AGA progresses. Other hair loss afflictions include alopecia arcata (AA), female pattern baldness and hair loss secondary to chemotherapy and/or radiation treatment (i.e., secondary alopecia). In the case of secondary alopecia, the peptide-copper complexes may be used in advance of certain hair-loss insults, such as chemotherapy or radiation regiments, to stimulating hair growth prior to the insult and thereby reduce the amount of hair loss resulting therefrom.

As mentioned above, the peptide-copper complexes of the present invention have at least two amino acids (or amino acid derivatives), one of which is histidine, arginine or a derivative thereof. In this context, the peptide-copper complexes have structure A as identified above. For example, when $R_1$ is an amino acid and $R_2$ is histidyl, or when $R_1$ is an amino acid and $R_2$ is arginine, the peptide copper complex has the following structures D and E, respectively:

D: [(amino acid)-histidine]:copper(II)

E: [(amino acid)-arginine]:copper(II)

As used in structure A above, the terms "amino acid" and "amino acid derivative" are defined hereinbelow. An amino acid of this invention includes any carboxylic acid having an amino moiety, including (but not limited to) the naturally occurring α-amino acids (in the following listing, the single letter amino acid designations are given in parentheses): alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y) and valine (V). Other naturally occurring amino acids include (but are not limited to) hydroxyproline and γ-carboxyglutamate. In a preferred embodiment, the amino acid is a naturally occurring α-amino acid having an amino moiety (i.e., the —$NH_2$ group, rather than a secondary amine, —NH—, such as present in proline) attached to the α-carbon of the amino acid which, when chelated to copper, occupies a coordination site thereof. As used herein, "hydrophillic amino acids" include (but are not limited to) the amino acids selected from K, R, H, D, E, N, Q, C, M, S and T.

An amino acid derivative of this invention includes any compound having the structure:

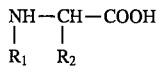

wherein R is a derivative of a naturally occurring amino acid side chain. In one embodiment, $R_1$ and $R_2$ in the above structure may be selected from hydrogen, a substituted or unsubstituted, straight chain, branched or cyclic, saturated or unsaturated alkyl moiety containing from 1–20 carbon atoms, and a substituted or unsubstituted aryl moiety containing from 6–20 carbon atoms (including heteroaromatic moieties). In a preferred embodiment, $R_1$ and $R_2$ may be selected from the chemical moieties identified in Table 1 below.

TABLE 1

Amino Acid Derivatives

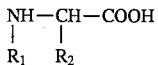

Where $R_2$=H or the following moieties:

—$(CH_2)_n CH_3$ where n=1–20

—$(CH_2)_n CH(CH_3)(CH_2)_m CH_3$ where n, m=0–20 (when n=0, m≠0 or 1 and when n=1, m≠0)

—$(CH_2)_n NH_2$ where n=1–20 (n≠4)

—$(CH_2)_n CONH_2$ where n=3–20

—$(CH_2)_n COOH$ where n=3–20

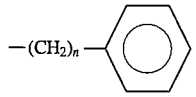

where n=2–20

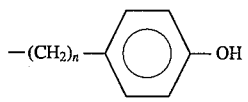

where N=2–20

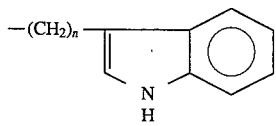

where N=2–20

—$(CH_2)_n SH$ where n=2–20

—$(CH_2)_n S(CH_2)_m CH_3$ where n, m=1–20 (when n=2, m≠0)

—$(CH_2)_n CH_2 OH$ where n=1–20

—$(CH_2)_n CH(CH_3)OH$ where n=1–20

And where $R_1$=H or the following moieties:

—$(CH_2)_n CH_3$ where n=0–20

—$(CH_2)_n CH(CH_3)(CH_2)_m CH_3$ where n, m=0–20

Histidine derivatives of this invention include compounds having the structure:

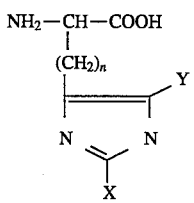

where n=1–20, and X and Y are independently selected from alkyl moieties containing from 1–12 carbon atoms or an aryl moiety containing from 6–12 carbon atoms. In preferred embodiments, n is 1, X is methyl and Y is H (i.e., 3-methyl histidyl) or X is H and Y is methyl (i.e., 5-methyl histidine).

Similarly, arginine derivatives of this invention include compounds having the structure:

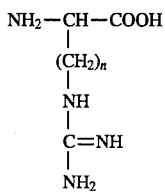

where n=1–20 (excluding n=3).

In another embodiment of this invention, the peptide-copper complexes of structure A further comprise a chemical moiety linked to the $R_2$ moiety by an amide or peptide bond. (i.e., —C(=O)NH—). The peptide-copper complexes of this embodiment are depicted above as structure B. As used herein, a chemical moiety (i.e., R3) linked to the $R_2$ moiety by an amide bond includes any chemical moiety having an amino group capable of forming an amide linkage with the carboxyl terminus of $R_2$ (i.e., the carboxyl terminus of histidine, arginine, or derivatives thereof). Suitable $R_3$ moieties include (but are not limited to) —$NH_2$, alkylamino moieties having from 1–20 carbon atoms and arylamino moieties having from 6–20 carbon atoms, as well as amino acids and derivatives thereof. As used herein, "alkylamino moieties" include alkyl moieties containing an amino moiety, wherein the alkyl moiety is as defined above, and includes (but is not limited to) octyl amine and propyl amine. Similarly, "arylamino moieties" include aryl moieties containing an amino moiety, wherein the aryl moiety is as defined above, and includes (but is not limited to) benzylamine and benzyl-$(CH_2)_{1-14}$-amine. Further examples of suitable chemical moieties having amino groups capable of forming an amide linkage with the carboxyl terminus of $R_2$ include polyamines such as spermine and sperimidine.

For example, in structure B when $R_1$ is an amino acid, $R_2$ is histidine or arginine, and $R_3$ is an amino moiety, the peptide-copper complex has the following structures F and G, respectively:

F: [(amino acid)-histidine-$NH_2$]:copper(II)
G: [(amino acid)-arginine-$NH_2$]:copper(II)

Similarly, when $R_1$ is an amino acid, $R_2$ is histidine or arginine, and $R_3$ is an alkylamino moiety, the peptide-copper complex has the following structures H and I, respectively:

H: [(amino acid)-histidine-NH-alkyl]:copper(II)
I: [(amino acid)-arginine-NH-alkyl]:copper(II)

In yet a further embodiment (as represented by structure C above), the $R_3$ moiety of structure B is at least one an amino acid or an amino acid derivative as defined above. In a preferred embodiment, $R_3$ is a naturally occurring α-amino acid joined to $R_2$ by a peptide bond. For example, when $R_1$ and $R_3$ of structure C are amino acids, and $R_2$ is histidine or arginine, the peptide-copper complexes of this invention have the following structures J and K, respectively:

J: [(amino acid)-histidine-(amino acid)]:copper(II)
K: [(amino acid)-arginine-(amino acid)]:copper(II)

It should be understood that while only a single amino acid is depicted in the $R_3$ position of structures H and I, other chemical moieties may also be present, including additional amino acids and/or amino acid derivatives. For example, $R_3$ in structures H and I may be a peptide such as phenylalanine-phenylalanine, (glycyl)$_n$-tryptophan where n=1–4, prolyl-$X_1$-phenylalanyl-$X_2$ or $X_1$-phenylalanyl-$X_2$ where $X_1$ and $X_2$ are selected from valine, alanine and glycine.

The peptides of the peptide-copper complexes of this invention may generally be classified as dipeptides (i.e, structure A), dipeptides with a chemical moiety attached to the carboxyl terminus via an amide bond (i.e., structure B) or as tripeptides (i.e., structure C above). In the case of peptide-copper complexes of structures B and C, additional chemical moieties, including amino acids, may be joined to the dipeptide or tripepride to yield peptides containing four or more amino acids. For purpose of illustration, Table 2 presents various representative examples of peptide-copper complexes of this invention.

TABLE 2

Representative Peptide-Copper Complexes

Structure A:

| | |
|---|---|
| glycyl-histidine:copper | alanyl-histidine:copper |
| glycyl-(3-methyl)histidine:copper | alanyl-(3-methyl)histidine:copper |
| glycyl-(5-methyl)histidine:copper | alanyl-(5-methyl)histidine:copper |
| glycyl-arginine:copper | alanyl-arginine:copper |
| (N-methyl)glycine-histidine:copper | (N-methyl)glycine-arginine:copper |

Structure B:

| | |
|---|---|
| glycyl-histidyl-$NH_2$:copper | glycyl-arginyl-$NH_2$:copper |
| glycyl-(3-methyl)histidyl-$NH_2$:copper | alanyl-(3-methyl)histidyl-$NH_2$:copper |
| glycyl-arginyl-$NH_2$:copper | alanyl-arginyl-$NH_2$:copper |
| (N-methyl)glycine-histidyl-$NH_2$:copper | (N-methyl)glycine-arginyl-$NH_2$:copper |
| glycyl-histidyl-NHoctyl:copper | glycyl-arginyl-NHoctyl:copper |

Structure C:

| | |
|---|---|
| glycyl-histidyl-lysine:copper | glycly-arginyl-lysine:copper |
| glycyl-(3-methyl)histidyl-lysine:copper | glycyl-(5-methyl)histidyl-lysine:copper |
| alanyl-histidyl-lysine:copper | alanyl-arginyl-lysine:copper |
| alanyl-(3-methyl)histidyl-lysine:copper | alanyl-(5-methyl)histidyl-lysine:copper |
| glycyl-histidyl-phenylalanine:copper | glycyl-arginyl-phenylalanine:copper |
| glycyl-(3-methyl)histidyl-phenylalanine:copper | glycyl-(5-methyl)histidyl-phenylalanine:copper |
| alanyl-histidyl-phenylalanine:copper | alanyl-arginyl-phenylalanine:copper |
| alanyl-(3-methyl)histidyl-phenylalanine:copper | alanyl-(5-methyl)histidyl-phenylalanine:copper |
| glycyl-histidyl-lysyl-phenylalanyl-phenylalanyl:copper | glycyl-arginyl-lysyl-phenylalanyl-phenylalanyl:copper |
| glycyl-(3-methyl)histidyl-lysyl-phenylalanyl-phenylalanyl:copper | glycyl-(5-methyl)histidyl-lysyl-phenylalanyl-phenylalanyl:copper |
| (N-methyl)glycyl-histidyl-lysine:copper | (N-methyl)glycyl-arginyl-lysine:copper |

Further examples of peptide-copper complexes of this invention are disclosed in U.S. Pat. Nos. 5,118,665 and 5,164,367, as well as U.S. Pat. Nos. 4,760,051; 4,665,054; 4,877,770; 5,177,061; 4,810,693; 4,767,753; 5,135,913; 5,023,237; 5,059,588 and 5,120,831, all of which are incorporated herein by reference in their entirety. Thus, the peptide-copper complexes disclosed in the above U.S. patents may be used to stimulate hair growth in animals (including humans) afflicted with androgenetic alopecia (AGA) or male pattern baldness, thereby eliminating or reducing the severity of hair loss and/or the speed at which AGA progresses. These peptide-copper complexes may also by used to treat other hair loss afflictions, include alopecia areata, female pattern baldness and hair loss secondary to chemotherapy and/or radiation treatment (i.e., secondary alopecia). In the case of secondary alopecia, the peptide-copper complexes may be used to stimulate hair growth prior to a insults which normally result in hair loss, such as chemotherapy or radiation regiments. Thus, the peptide-copper complexes of this invention may be used to prevent hair loss.

In the practice of this invention, the molar ratio of peptide to copper is greater than zero to one (e.g., 0.1:1, 0.2:1, etc.). The molar ratio of peptide to copper will depend, in part, on the number of copper coordination sites that are occupied by the peptide. In a preferred embodiment, the molar ratio of peptide to copper ranges from about 1:1 to 3:1, and more preferably from about 1:1 to 2:1. For example, in the case of a tripeptide (such as GHF:copper), the preferred ratio of peptide to copper ranges from 1:1 to 2:1, with each tripeptide occupying three coordination sites of the copper. Similarly, with a dipeptide (such as GH:copper), the preferred ratio of peptide to copper ranges from 1:1 to 3:1, with each dipeptide occupying two coordination sites of copper ion.

In another embodiment of this invention, a chelating agent may be added to the peptide-copper complex to form a ternary peptide-copper-chelating agent complex. Suitable chelating agents include imidazole or imidazole-containing compounds, such as histidine, and sulfur containing amino acids, such as cysteine or methionine. Thus, if the peptide-copper complex is GHF:copper, histidine may be added to yield the ternary complex GHF:copper:histidine. However, to form such a ternary complex, the molar ratio of copper to peptide to chelating agent must be considered. For example, if the ratio of peptide to copper is 2:1, the addition of a chelating agent to the peptide-copper complex, although possible, is difficult due to site occupancy by the peptide. However, by maintaining the ratio of peptide to copper near 1:1, a chelating group may readily be added to form the ternary complex. Thus, the preferred peptide to copper to chelating agent ratio is about 1:1:1.

While the chiral amino acids of the present invention (particularly the amino acids) have not been specifically designated, the present invention encompasses both the naturally occurring L-form, as well as the D-form. For example, any of the naturally occurring L-amino acids (or amino acid derivatives) disclosed herein may be replaced by a corresponding D-amino acid (or amino acid derivative).

In the practice of this invention, it is critical that the second position of the peptide (i.e., $R_2$ of structures A, B and C) is either histidine, arginine or a derivative thereof. It is believed that the superior effect of the peptide-copper complexes of the present invention is achieved, at least in part, by the binding of copper by an amino moiety of the amino acid side chain of histidine, arginine or derivitive thereof. For example, in the case of histidine, an amine group of the histidine imidazole ring occupies a coordination site of the copper (i.e., the residual valencies or unshared electrons of the amine group are shared with copper). In the case of arginine, an amine group of the amino acid side chain similarly occupies a coordination site of copper. The binding of $R_2$ to the copper atom is preferably combined with the coordination of an amine group from the $R_1$ moiety of structures A, B and C, to yield the peptide-copper complex. Thus, a peptide of this invention chelates copper by donating the $R_2$ amine group, and preferably both the $R_1$ and $R_2$ amine groups, to the peptide-copper complex. The peptide-copper complexes of structures B and C can further occupy additional coordination sites on copper. Specifically, the amine group of the amide bond of structure B and the peptide bond of structure C can occupy yet a further coordination sites.

As mentioned above, the peptide-copper complexes of this invention have utility as hair growth agents. More particularly, the peptide-copper complexes stimulates hair growth on warm-blooded animals. Thus, the peptide-copper complexes may be used to treat a variety of diseases states associated with hair loss, including (but not limited to) androgenetic alopecia (also know as male pattern baldness), alopecia areata and female pattern baldness. In these instances, the peptide-copper complexes stimulates the growth of hair after the onset of the hair-loss affliction. Alternatively, the peptide-copper complexes may be administered prophylactically for conditions such as secondary alopecia. For example, the complexes may be administered prior to an insult which normally results in hair loss, such as chemotherapy and/or radiation treatment. Thus, the peptide-copper complexes of this invention can be used to prevent hair loss.

Administration of the peptide-copper complexes of the present invention may be accomplished in any manner which will result in the delivery of an effective amount or dose of the peptide-copper complex to the animal, including delivery to the hair follicles. For example, administration may be by topical application directly to the scalp, or other area where hair stimulation is desired (hereinafter "the treatment area"). Alternatively, administration may also be accomplished by injection (such as intradermal injection) into the treatment area, including the scalp. Typically, the peptide-copper complexes are formulated as a composition containing the peptide-copper complex in combination with on or more acceptable carriers or diluents, including formulations which provide for the sustained release of the peptide-copper complexes over time.

In one embodiment, the peptide-copper complexes are formulated for intradermal injection to the treatment area. In such instances, such formulations preferably contain one or more peptide-copper complexes of this invention in combination with a suitable vehicle for intradermal injection, with the peptide-copper complex present in the composition at a concentration ranging from 100 µg to 2000 µg per 0.1 ml vehicle (i.e., 1.0 mg/ml to 20 mg/ml). Suitable vehicles for intradermal injection include (but are not limited to) saline and sterile water.

In another embodiment, the peptide-copper complexes are formulated for topical administration. Suitable topical formulations include one or more peptide-copper complexes in the form of a liquid, lotion, cream or and gel. Topical administration may be accomplished by application directly on the treatment area. For example, such application may be accomplished by rubbing the formulation (such as a lotion or gel) onto the skin of the treatment area, or by spray application of a liquid formulation onto the treatment area. Any quantity of the topical formulation sufficient to accelerate the rate of hair growth or prevent subsequent hair loss is effective, and treatment may be repeated as often as the progress of hair growth indicates. Preferable, the topical compositions of this invention contain one or more peptide-copper complexes in an amount ranging from 0.1% to 20% by weight of the composition, and more preferably from 0.1% to 5% by weight of the composition.

In addition to carriers and diluents, the peptide-copper complexes may also be formulated to contain additional ingredients such as penetration enhancement agents and/or surface active agents. For example, topical formulations may contain 0.5% to 10% of one or more surface active agents (also called emulsifying agents). Non-ionic surface active agents and ionic surface active agents may be used for the purposes of the present invention. Examples of suitable non-ionic surface active agents are nonylphenoxypolyethoxy ethanol (Nonoxynol-9), polyoxyethylene oleyl ether (Brij-97), various polyoxyethylene ethers (Tritons), and block copolymers of ethylene oxide and propylene oxide of various molecular weights (such as Plutonit 68). Examples of suitable ionic surface active agents include sodium lauryl sulfate and similar compounds. Penetration enhancing agents may be also be present in topical formulations. Suitable penetration enhancing agents include dimethyl sulfoxide (DMSO), urea and substituted urea compounds. In the case of a liquid formulation for topical administration, the concentration of the penetrating enhancing agent (such as DMSO) may range from 30% to 80% of liquid formulation.

The balance of the topical formulations may include inert, physiologically acceptable carriers or diluents. Suitable carriers or diluents include, but are not limited to, water, physiological saline, bacteriostatic saline (saline containing 0.9 mg/ml benzyl alcohol), petrolatum based creams (e.g., USP hydrophilic ointments and similar creams, Unibase, Parke-Davis, for example), various types of pharmaceutically acceptable gels, and short chain alcohols and glycols (e.g., ethyl alcohol and propylene glycol). In another embodiment of the invention, topical formulations may also contain the peptide-copper complex encapsulated in liposomes to aid in the delivery of the peptide-copper complex to the hair follicle. Alternatively, the peptide-copper complex may be formulated in an instrument to deliver the compound via iontophoresis.

The peptide-copper complexes of this invention exhibit superior skin permeability when applied topically. This results in a greater effective dose to the treatment area, and thus correspondingly greater stimulation of hair growth. In the practice of this invention, hydrophobic amino acids or amino acid derivatives are preferably used for administration by injection (such as intradermal injection), while hydrophilic amino acids or amino acid derivatives are used for topical administration. While the use of hydrophobic amino acids or amino acid derivatives generally enhance activity of the copper-peptide complexes of this invention, the use of hydrophilic amino acids or amino acids derivatives for topical administration is preferred due to the enhanced skin permeability associated therewith.

For purpose of illustration, Table 3 presents examples of suitable topical formulations within the context of the present invention. As used below, "% (w/w)" represents the weight percentage of a component based on the total weight of the formulation:

TABLE 3

| Representative Topical Formulations | |
|---|---|
| Preparation A: | |
| Peptide-Copper Complex | 1.0% (w/w) |
| Hydroxy Ethyl Cellulose | 3.0% (w/w) |
| Propylene Glycol | 20.0% (w/w) |
| Nonoxynol-9 | 3.0% (w/w) |
| Benzyl Alcohol | 2.0% (w/w) |
| Aqueous Phosphate Buffer (0.2N) | 71.0% (w/w) |

TABLE 3-continued

| Representative Topical Formulations | |
|---|---|
| Preparation B: | |
| Peptide-Copper Complex | 1.0% (w/w) |
| Nonoxynol-9 | 3.0% (w/w) |
| Ethyl Alcohol | 96.0% (w/w) |
| Preparation C: | |
| Peptide-Copper Complex | 5.0% (w/w) |
| Ethyl Alcohol | 47.5% (w/w) |
| Isopropyl Alcohol | 4.0% (w/w) |
| Propylene Glycol | 20.0% (w/w) |
| Lanoeth-4 | 1.0% (w/w) |
| Water | 27.5% (w/w) |
| Preparation D: | |
| Peptide-Copper Complex | 5.0% (w/w) |
| Sterile Water | 95.0% (w/w) |
| Preparation E: | |
| Peptide-Copper Complex | 2.5% (w/w) |
| Hydroxypropyl Cellulose | 2.0% (w/w) |
| Glycerine | 20.0% (w/w) |
| Nonoxynol-9 | 3.0% (w/w) |
| Sterile Water | 72.5% (w/w) |
| Preparation F: | |
| Peptide-Copper Complex | 0.5% (w/w) |
| Sterile Water | 16.5% (w/w) |
| Propylene Glycol | 50.0% (w/w) |
| Ethanol | 30.0% (w/w) |
| Nonoxynol-9 | 3.0% (w/w) |
| Preparation G: | |
| Peptide-Copper Complex | 5.0% (w/w) |
| Sterile Water | 10.0% (w/w) |
| Hydroxypropyl Cellulose | 2.0% (w/w) |
| Propylene Glycol | 30.0% (w/w) |
| Ethanol | 50.0% (w/w) |
| Nonoxynol-9 | 3.0% (w/w) |

The peptides of the present invention may be synthesized by either solution or solid phase techniques known to one skilled in the art of peptide synthesis. The general procedure involves the stepwise addition of protected amino acids to build up the desired peptide sequence. The resulting peptide may then be complexed to copper (at the desired molar ratio of peptide to copper) by dissolving the peptide in water, followed by the addition of copper chloride and adjusting the pH. A more detailed disclosure directed to the synthesis of the peptide-copper complexes of this invention, as well as the activity certain representative peptide-copper complexes, are presented below.

EXAMPLES

The following examples are offered by way of illustration, and not by way of limitation. To summarize the examples that follow, Example 1 discloses the general preparation of peptide-copper complexes of the present invention by chelating a peptide to copper in an aqueous solution. Examples 2–10 disclose the synthesis of peptides which may be chelated to copper to yield peptide-copper complexes. Examples 11–16 disclose the ability of representative peptide-copper complexes of this invention to stimulate hair growth.

Source of Chemicals

Chemicals and peptide intermediates utilized in the following examples may be purchased from a number of suppliers, including: Sigma Chemical So., St. Louis, Mo.; Peninsula Laboratories, San Carlos, Calif.; Aldrich Chemical Company, Milwaukee, Wis.; Vega Biochemicals, Tucson, Ariz.; Pierce Chemical Co., Rockford, Ill.; Research Biochemicals, Cleveland, Ohio; Van Waters and Rogers, South San Francisco, Calif.; and Bachem, Inc., Torrance, Calif.

EXAMPLE 1

Preparation of Peptide-Copper Complex

The peptide-copper complexes of the present invention may be synthesized by dissolving the peptide in distilled water, followed by the addition of copper chloride (e.g., 99.999% available from Chemical Dynamics, N.J.) and then adjusting the pH of the solution to about 7.0. For example, copper complexes of glycyl-L-histidyl-L-phenylalanine (GHF) with a molar ratio of peptide to copper of 1:1, 2:1, or greater (e.g., 3:1), may be prepared by dissolving a given weight of GHF in distilled water (e.g., 50 mg/ml), and adding the desired molar amount of purified copper-chloride. The pH of the resulting peptide solution is then adjusted to about 7.0 by the addition of, for example, a sodium hydroxide solution. Alternatively, copper salts other than copper chloride may be used, for example, copper acetate, copper sulfate or copper nitrate.

EXAMPLE 2

Synthesis of Glycyl-L-Histidyl-L-Caprolactam

L(-)-3-amino-ε-caprolactam was dissolved in tetrahydrofuran (THF) then coupled with $N^\alpha$-t-butyloxycarbonyl-$N^{im}$-benzyloxycarbonyl-L-histidine ($N^\alpha$-BOC-$^{im}$-CBZ-L-histidine) using isobutyl chloroformate and N-methylmorpholine in THF. After two hours at −20° C. and an additional hour at ambient temperature, the reaction was quenched with 2N aqueous potassium bicarbonate. This product was extracted into ethyl acetate, washed with 1M aqueous citric acid, and saturated sodium bicarbonate. The organic phase was dried over anhydrous sodium sulfate. Filtration and evaporation gave $N^\alpha$-BOC-$N^{im}$-CBZ-L-histidyl-L-caprolactam.

The above compound was dissolved in 30% trifluoroacetic acid in dichloromethane for 30 minutes, then evaporated, forming $N^{im}$-benzyloxycarbonyl-L-histidyl-L-caprolaetam. This was then dissolved in chloroformate, N-methylmorpholine and benzyloxycarbonyl-glycine were added to form benzyloxycarbonyl-glycyl-$N^{im}$-benzyloxycarbonyl-L-histidyl-L-caprolactam. This product was recrystallized once from ethyl acetate then dissolved in acetic acid and hydrogenated overnight in the presence of 10% Pd-C catalyst. The resultant glycyl-L-histidyl-L-caprolactam was lyophilized from water several times, then purified by liquid chromatography on a C-18 reverse-phase column to yield the peptide as a diacetate salt.

EXAMPLE 3

Synthesis of L-Alanyl-L-Histidyl-L-Phenylalanine

To a stirred solution of $N^\alpha$-BOC-$N^{im}$-CBZ-L-histidine (9.74 g, 25.0 mmol) and N-methylmorpholine (5.8 mL, 5.3 g, 52.5 mmol) in tetrahydrofuran (50 mL) at −15° C. was added isobutyl chloroformate (3.4 mL, 3.6 g, 26.3 mmol). After 2 min. phenylalanine benzyl ester tosylate (10.7 g, 25.0 mmol) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M KHCO$_3$ (3×100 mL), water, and brine. The resulting solution was dried over sodium sulfate, filtered, and evaporated to give 13.7 g (87%) of the blocked dipeptide as a white semi-solid ($R_f$=0.75, 10% methanol/dichloromethane), which was used in the following transformation without further purification.

A solution of the t-butyloxycarbonyl protected dipeptide (12.9 g, 20.6 mmol) in 35% trifluoroacetic acid/dichloromethane (150 mL) was stirred ½ h at room temperature. The resulting solution was concentrated in vacuo and neutralized with 2M aqueous potassium bicarbonate. The product was extracted into ethyl acetate (3×150 mL). The combined extracts were dried over sodium sulfate, filtered, and evaporated to give 13.3 g (ca. 100%+entrained solvent) of the free-amino compound as a white solid: $R_f$=0.49 (10% methanol/dichloromethane).

To a stirred solution of N-CBZ-L-alanine (6.03 g, 27.0 mmol) and N-methylmorpholine (3.3 mL, 3.0 g, 29.7mmol) in tetrahydrofuran (50 mL) at −15° C. was added isobutyl chloroformate (3.7 mL, 3.9 g, 28.4 mmol). After 2 min. a solution of the suitably protected dipeptide (11.4 g, 21.8 mmol) in tetrahydrofuran (50 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×100 mL). The combined extracts were washed with 1M citric acid (3×100 mL), water, 2M KHCO$_3$ (3× 100 mL), water, and brine. The resulting solution was dried over sodium sulfate, filtered, and evaporated to give the blocked tripeptide as a white solid ($R_f$=0.55, 10% methanol/dichloromethane), which was recrystallized from 95% ethanol to give 12.6 g (79%) of a free-flowing white powder: mp 147°–147.5° C.; Anal. Calcd. for $C_{41}H_{40}N_5O_8$: C, 67.39; H, 5.52; N, 9.58. Found: C, 66.78; H, 5.64; N, 9.24.

To a suspension of the blocked tripeptide (12.6 g, 17.6 mmol) in ethanol (150 mL) was added water, until the mixture became very turbid (about 150 mL). The resulting mixture was shaken with palladium chloride (1.56 g, 8.8 mmol) under an atmosphere of hydrogen (5 atm) for 16 h. The catalyst was removed by filtration through a plug of Celite® and the flitrate was concentrated to remove volatile organic materials. The remainder was lyophilized to give 8.30 g of white powder. This material was dissolved in water, filtered through a 0.2 m nylon membrane and lyophilized to give 6.27 g (87%) of the desired tripepride dihydrochlofide as a free-flowing white powder: $[a]_D$5.1° (c 2.0, water); $^1$H NMR (500 MHz, DMSO-d$_6$) d 8.71 (1H, d, J=7.9), 8.49 (1H, d, J=7.8), 8.21 (1H, s), 7.30–7.22 (4H, m), 7.20–7.15 (1H, m), 7.12 (1H, s), 4.54 (1H, br q, J=7.1), 4.37 (1H, m), 3.86 (1H, q, J=6.8), 3.12 (1H, dd, J=4.3, 13.8), 3.05–2.90 (2H, m), 2.88 (1H, dd, J=9.5, 13.8), 1.27 (3H, d, J=6.8); $^{13}$C NMR (125 MHz, DMSO-d$_6$) d 173.5, 169.9, 169.5, 138.1, 134.2, 130.5, 129.2, 128.2, 126.4, 117.8, 54.4, 52.5, 48.0, 36.8, 28.5, 17.2.

EXAMPLE 4

Synthesis of Glycyl-L-Histidyl-L-Glutamic Acid

To a stirred solution of $N^\alpha$-BOC-$N^{im}$-CBZ-L-histidine (9.74 g, 25.0 mmol) and N-methylmorpholine (5.8 mL, 5.3 g, 52.5 mmol) in tetrahydrofuran (50 mL) at −15° C. was added isobutyl chloroformate (3.4 mL, 3.6 g, 26.3 mmol). After 2 min. glutantic acid dibenzyl ester tosylate (12.5 g, 25.0 mmol) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M KHCO$_3$ (3×100 mL), water, and brine. The resulting solution was dried over sodium sulfate, filtered, and evaporated to give 15.2 g (87%) of the blocked dipeptide as a white semi-solid (R$_f$=0.74, 10% methanol/dichloromethane), which was used in the following transformation without further purification.

A solution of the t-butyloxycarbonyl protected dipeptide (15.1 g, 21.6 mmol) in 35% trifluoroacetic acid/dichloromethane (150 mL) was stirred ½ h at room temperature. The resulting solution was concentrated in vacuo and neutralized with 2M aqueous potassium bicarbonate. The product was extracted into ethyl acetate (3×150 mL). The combined extracts were dried over sodium sulfate, filtered, and evaporated to give 14.8 g (ca. 100% +entrained solvent) of the free-amino compound as a white solid: R$_f$=0.48 (10% methanol/dichloromethane).

To a stirred solution of N-CBZ-glycine (5.23 g, 25.0 mmol) and N-methylmorpholine (3.0 mL, 2.8 g, 27.5 mmol) in tetrahydrofuran (50 mL) at −15° C. was added isobutyl chloroformate (3.4 mL, 3.6 g, 26.3 mmol). After 2 min. a solution of the suitably protected dipeptide (12.9 g, 21.6 mmol) in tetrahydrofuran (50 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×100 mL). The combined extracts were washed with 1M citric acid (3×100 mL), water, 2M KHCO$_3$ (3×100 mL), water, and brine. The resulting solution was dried over sodium surfate, filtered, and concentrated to a syrup, which was diluted with absolute ethanol, and kept overnight at −20° C. The resulting precipitate was collected on a filter to afford 9.93 g (58%) of the blocked tripeptide as a white solid (R$_f$=0.58, 10% methanol/dichloromethane): mp 114°–116° C. Anal. Calcd. for C$_{43}$H$_{43}$N$_5$O$_{10}$: C, 65.39; H, 5.49; N, 8.87. Found: C, 64.93; H, 5.56; N, 8.41.

To a suspension of the blocked tripepride (9.6 g, 12.2 mmol) in ethanol (150 mL) was added water, until the mixture became very turbid (about 150 mL). The resulting mixture was shaken with palladium chloride (2.22 g, 12.5 mmol) under an atmosphere of hydrogen (5 atm) for 16 h. The catalyst was removed by filtration through a plug of Celite® and the filtrate was concentrated to remove volatile organic materials. The remainder was lyophilized to give 4.72 g of white powder. This material was dissolved in water, filtered through a 0.2 m nylon membrane and lyophilized to give 4.64 g (93%) of the desired tripeptide dihydrochloride as a free-flowing white powder: [a]$_D$ −16.6° (c 2.0, water); $^1$H NMR (500 MHz, D$_2$O) d 8.65 (1H, s), 7.35 (1H, s), 4.77 (1H, m), 4.46 (1H, m), 3.88 (2H, s), 3.28 (1H, dd, J=15.3, 6.1), 3.21 (1H, dd, J=15.3, 8.0), 2.47 (2H, m), 2.21 (2H, m), 2.00 (2H, m); $^{13}$C NMR (125 MHz, D$_2$O) d 179.9, 177.3, 174.3, 169.8, 136.5, 130.8, 120.4, 55.6, 54.9, 43.3, 32.8, 29.3, 28.5; Anal. Calcd for C$_{13}$H$_{21}$Cl$_2$N$_5$O$_6$: C, 37.69; H, 5.11; N, 16.91; Cl, 17.12. Found: C, 37.23; H, 5.07; N, 16.01; Cl, 17.95.

EXAMPLE 5

Synthesis of Glycyl-L-Histidyl-L-Phenylalanine

To a stirred solution of N$^\alpha$-BOC-N$^{im}$-CBZ-L-histidine (9.74 g, 25.0 mmol) and N-methylmorpholine (5.8 mL, 5.3 g, 52.5 mmol) in tetrahydrofuran (50 mL) at −15° C. was added isobutyl chloroformate (3.4 mL, 3.6 g, 26.3 mmol). After 2 min. phenylalanine benzyl ester tosylate (10.7 g, 25.0 mmol) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M KHCO$_3$ (3×100 mL), water, and brine. The resulting solution was dried over sodium sulfate, filtered, and evaporated to give 13.0 g (83%) of the blocked dipeptide as a white semi-solid (R$_f$=0.79, 10% methanol/dichloromethane), which was used in the following transformation without further purification.

A solution of the t-butyloxycarbonyl protected dipeptide (12.9 g, 20.6 mmol) in 35% tfifiuoroacetic acid/dichloromethane (150 mL) was stirred ½ h at room temperature. The resulting solution was concentrated in vacuo and neutralized with 2M aqueous potassium bicarbonate. The product was extracted into ethyl acetate (3×150 mL). The combined extracts were dried over sodium sulfate, filtered, and evaporated to give 12.3 g (ca. 100%+entrained solvent) of the free-amino compound as a white solid: R$_f$=0.50 (10% methanol/dichloromethane).

To a stirred solution of N-CBZ-glycine (5.23 g, 25.0 mmol) and N-methylmorpholine (3.0 mL, 2.8 g, 27.5 mmol) in tetrahydrofuran (50 mL) at −15° C. was added isobutyl chloroformate (3.4 mL, 3.6 g, 26.3 mmol). After 2 min. a solution of the suitably protected dipeptide (10.8 g, 20.6 mmol) in tetrahydrofuran (50 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×100 mL). The combined extracts were washed with 1M citric acid (3×100 mL), water, 2M KHCO$_3$(3×100 mL), water, and brine. The resulting solution was dried over sodium sulfate, filtered, and evaporated to give 14.0 g (95%) of the blocked tripepride as a white solid (R$_f$=0.64, 10% methanol/dichloromethane), which was recrystallized from absolute ethanol to give a free-flowing white powder.

To a suspension of the blocked tripeptide (6.0 g, 8.3 mmol) in ethanol (150 mL) was added water, until the mixture became very turbid (about 150 mL). The resulting mixture was shaken with palladium chloride (1.47 g, 8.3 mmol) under an atmosphere of hydrogen (5 atm) for 16 h. The catalyst was removed by filtration through a plug of Celite® and the flitrate was concentrated to remove volatile organic materials. The remainder was lyophilized to give 1.46 g of white powder. This material was dissolved in water, filtered through a 0.2 m nylon membrane and lyophilized to give 1.38 g (38%) of the desired tripepride dihydrochloride as a free-flowing white powder: [a]$_D$−7.5° (c 1.0, water); $^1$H NMR (500 MHz, D$_2$O) d 8.59 (1H, s), 7.39–7.25 (5H, m), 7.21 (1H, s), 4.70 (1H, br t, J=7), 3.80 (2H, s), 3.24 (1H, dd, J=14.0, 5.5), 3.16 (1H, dd, J=15.4, 6.9), 3.10 (1H, dd, J=15.4, 7.4), 3.03 (1H, dd, J=14.0, 9.1); $^{13}$C NMR (125 MHz, DMSO-d$_6$) d 172.7, 169.5, 166.0, 137.6, 133.3, 129.2, 128.9, 128.3, 126.5, 116.8, 53.9, 51.8, 40.1, 36.4, 27.3.

EXAMPLE 6

Synthesis of Glycyl-L-Histidyl-L-Lysyl-L-Phenylalanine

To a stirred solution of N$^\alpha$-BOC-N$^{im}$-CBZ-L-lysine (9.5 g, 25.0 mmol) and N-methylmorpholine (5.8 mL, 5.3 g, 52.5 mmol) in tetrahydrofuran (50 mL) at −15° C. was added isobutyl chloroformate (3.4 mL, 3.6 g, 26.7 mmol). After 2 min. phenylalanine benzyl ester rosylate (10.7 g, 25.0 mmol) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M KHCO$_3$ (3×100 mL), water, and brine. The resulting solution was dried over sodium sulfate, filtered, and evaporated to give 17.76 g (ca. 100%+entrained solvent) of the blocked dipeptide as a white solid ($R_f$=0.84, 10% methanol/dichloromethane), which was used in the following transformation without further purification.

A solution of the t-butyloxycarbonyl protected dipeptide (15.4 g, 25.0 mmol) in 35% trifluoroacetic acid/dichloromethane (150 mL) was stirred ½ h at room temperature. The resulting solution was concentrated in vacuo and neutralized with 2M aqueous potassium bicarbonate. The product was extracted into ethyl acetate (3×100 mL). The combined extracts were dried over sodium sulfate, filtered, and evaporated to give 15.8 g (ca. 100%+entrained solvent) of the free-amino compound as a white semi-solid: $R_f$=0.55 (10% methanol/dichloromethane).

To a stirred solution of N$^\alpha$-BOC-N$^{im}$-CBZ-L-histidine (9.74 g, 25.0 mmol) and N-methylmorpholine (3.0 mL, 2.8 g, 27.5 mmol) in tetrahydrofuran (50 mL) at −15° C. was added isobutyl chloroformate (3.4 mL, 3.6 g, 26.7 mmol). After 2 min. a solution of the suitably protected dipeptide (12.9 g, 25.0 mmol) in tetrahydrofuran (30 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M KHCO$_3$ (3× 100 mL), water, and brine. The resulting solution was dried over sodium sulfate, filtered, and evaporated to give 20.58 g (93%) of the blocked tripeptide as a white semi-solid ($R_f$=0.67, 10% methanol/dichloromethane), which was used in the following transformation without further purification.

A solution of the t-butyloxycarbonyl protected tripeptide (20.5 g, 23.1 mmol) in 35% trifluoroacetic acid/dichloromethane (150 mL) was stirred ½ h at room temperature. The resulting solution was concentrated in vacuo and neutralized with 2M aqueous potassium bicarbonate. The product was extracted into ethyl acetate (3×150 mL). The combined extracts were dried over sodium sulfate, filtered, and evaporated to give 20.5 g (ca. 100%+entrained solvent) of the free-amino compound as a white solid: $R_f$=0.51 (10% methanol/dichloromethane).

To a stirred solution of N-CBZ-glycine (7.24 g, 34.6 mmol) and N-methylmorpholine (4.2 mL, 3.9 g, 38.1 mmol) in tetrahydrofuran (50 mL) at −15° C. was added isobutyl chloroformate (4.7 mL, 5.0 g, 36.3 mmol). After 2 min. a solution of the suitably protected tripeptide (18.2 g, 23.1 mmol) in 1:1 tetrahydrofuran/dimethylformamide (50 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M KHCO$_3$(3×100 mL), water, and brine. The resulting solution was dried over sodium sulfate, filtered, and evaporated to give 21.6 g (95%) of the blocked tetrapeptide as a white solid ($R_f$=0.85, 10% methanol/dichloromethane), which was used in the following transformation without further purification.

To a suspension of the blocked tetrapeptide (21.5 g, 21.9 mmol) in ethanol (150 mL) was added water, until the mixture became very turbid (about 125 mL). The resulting mixture was shaken with palladium chloride (3.89 g, 21.9 mmol) under an atmosphere of hydrogen (5 atm) for 16 h. The reaction mixture became clear within about ½ h, which may indicate completion of the reaction. The catalyst was removed by filtration and the filtrate was evaporated to give 13.7 g of colorless semi-solid. This material was dissolved in water and lyophilized to give 11.5 g (94%) of the desired tetrapeptide dihydrochloride as a free-flowing white powder: [a]$_D$−12.4° (c 2.0, H$_2$O); $^1$H NMR (500 MHz, D$_2$O) d 8.72 (1H, d, J=7.7), 8.40 (1H, d, J=7.8), 8.00 (1H, s) 7.30–7.19 (5H, m), 7.01 (1H, s), 4.62 (1H, br q, J=4.7), 4.44 (1H, m), 4.22 (1H, br, q, J=4.9), 3.58 (2H, s), 3.10–2.90 (4H, m), 2.72 (2H, t, J=7.3), 1.65–1.20 (6H, m).

EXAMPLE 7

Synthesis of Glycyl-L-Histidyl-L-Lysyl-L-Phenylalanyl-L-Phenylalanine

To a stirred solution of N$^\alpha$-BOC-L-phenylalanine (10.6 g, 40.0 mmol) and N-methylmorpholine (4.8 mL, 4.5 g, 44.0 mmol) in tetrahydrofuran (50 mL) at −15° C. was added isobutyl chloroformate (5.5 mL, 5.7 g, 42.0 mmol). After 2 min. a solution prepared by mixing phenylalanine benzyl ester tosylate (17.1 g, 40.0 mmol), tetrahydrofuran (50 mL), and N-methylmorpholine (4.4 mL, 4.08, 40.0 mmol) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M KHCO$_3$ (3×100 mL), water, and brine. The resulting solution was dried over sodium sulfate, filtered, and evaporated to give 19.8 g (98%) of the blocked dipeptide as a white solid ($R_f$=0.98, 10% methanol/dichloromethane).

A solution of the t-butyloxycarbonyl protected dipeptide (19.7 g, 39.2 mmol) in 35% trifluoroacetic acid/dichloromethane (150 mL) was stirred ½ h at room temperature. The resulting solution was concentrated in vacuo and neutralized with 2M aqueous potassium bicarbonate. The product was extracted into ethyl acetate (3×100 mL). The combined extracts were dried over sodium sulfate, filtered, and evaporated to give 19.3 g (ca. 100%+entrained solvent) of the free-amino compound: $R_f$=0.65 (10% methanol/dichloromethane).

To a stirred solution of N$^\alpha$-BOC-N$^{im}$-CBZ-L-lysine (15.2 g, 40.0 mmol) and N-methylmorpholine (4.8 mL, 4.5 g, 44.0 mmol) in tetrahydrofuran (100 mL) at −15° C. was added isobutyl chloroformate (5.5 mL, 5.7 g, 42.0 mmol). After 2 min. the protected dipeptide (15.8 g, 39.2 mmol) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M KHCO$_3$ (3×100 mL), water, and brine. The resulting solution was dried over sodium sulfate, filtered, and evaporated to give 29.9 g (98%) of the blocked tripepride as a white solid ($R_f$=0.84, 10% methanol/dichloromethane).

A solution of the t-butyloxycarbonyl protected tripepride (15.4 g, 25.0 mmol) in 35% tfifiuoroacetic acid/dichloromethane (300 mL) was stirred ½ h at room temperature.

The resulting solution was concentrated in vacuo and neutralized with 2M aqueous potassium bicarbonate. The product was extracted into ethyl acetate (3×100 mL). The combined extracts were dried over sodium sulfate, filtered, and evaporated to give 28.7 g (ca. 100%+entrained solvent) of the free-amino compound as a fluffy white solid: $R_f$=0.72 (10% methanol/dichloromethane).

To a stirred solution of $N^\alpha$-BOC-$N^{im}$-CBZ-L-histidine (15.6 g, 40.0 mmol) and N-methylmorpholine (4.8 mL, 4.5 g, 44.0 mmol) in tetrahydrofuran (80 mL) at −15° C. was added isobutyl chloroformate (5.5 mL, 5.7 g, 42.0 mmol). After 2 min. a solution of the suitably protected tripeptide (12.9 g, 25.0 mmol) in dimethylformamide (50 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M $KHCO_3$ (3× 100 mL), water, and brine. The resulting solution was dried over sodium sulfate, filtered, and evaporated to give 29.1 g (72%) of the blocked tetrapeptide as a white solid ($R_f$=0.97, 10% methanol/dichloromethane).

A solution of the t-butyloxycarbonyl protected tetrapeptide (29.1 g, 28.0 mmol) in 35% trifluoroacetic acid/dichloromethane (300 mL) was stirred ½ h at room temperature. The resulting solution was concentrated in vacuo and neutralized with 2M aqueous potassium bicarbonate. The product was extracted into ethyl acetate (3×150 mL). The combined extracts were dried over sodium sulfate, filtered, and evaporated to give 28.4 g (ca. 100%+entrained solvent) of the free-amino compound as a white solid.

To a stirred solution of N-CBZ-glycine (7.32 g, 35.0 mmol) and N-methylmorpholine (4.2 mL, 3.9 g, 38.1 mmol) in tetrahydrofuran (100 mL) at −15° C. was added isobutyl chloroformate (4.8 mL, 5.0 g, 36.7 mmol). After 2 min. a solution of the suitably protected tetrapeptide (26.3 g, 28.0 mmol) in 1:1 tetrahydrofuran/dimethylformamide (50 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M $KHCO_3$ (3×100 mL), water, and brine. The resulting solution was dried over sodium sulfate, filtered, and evaporated to give 27.3 g (87%) of the blocked pentapeptide as a white solid ($R_f$=0.95, 10% methanol/dichloromethane).

To a suspension of the blocked pentapeptide (27.3 g, 24.2 mmol) in ethanol (200 mL) was added water, until the mixture became very turbid (about 100 mL). The resulting mixture was shaken with palladium chloride (4.3 g, 24.4 mmol) under an atmosphere of hydrogen (5 atm) for 16 h. The reaction mixture became clear within about ½ h, which may indicate completion of the reaction. The catalyst was removed by filtration and the flitrate was evaporated to give 14.6 g (82%) of the desired pentapeptide dihydrochloride as a free-flowing white powder: $[a]_D$−12.1°(c 2.0, methanol).

EXAMPLE 8

Synthesis of Glycyl-L-Arginyl-L-Lysine

To a stirred solution of $N^\alpha$-BOC-$N^g$-nitro-L-arginine (8.0 g, 25.0 mmol) and N-methylmorpholine (3.0 mL, 2.8 g, 27.5 mmol) in tetrahydrofuran (50 mL) at −15° C. was added isobutyl chloroformate (3.4 mL, 3.6 g, 26.3 mmol). After 2 min. a solution of L-(N $^{im}$-CBZ)lysine benzyl ester hydrochloride (10.2 g, 25.0 mmol) and N-methylmorpholine (2.8 mL, 2.5 g, 25.0 mmol) in tetrahydrofuran (30 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M $KHCO_3$ (3×100 mL), water, and brine. The resulting solution was dried over sodium sulfate, filtered, and evaporated to give 16.3 g (97%) of the blocked dipeptide as a white solid ($R_f$=0.57, 10% methanol/dichloromethane).

A solution of the t-butyloxycarbonyl protected dipeptide (16.3 g, 24.3 mmol) in 35% trifluoroacetic acid/dichloromethane (150 mL) was stirred for ½ h at room temperature. The resulting solution was concentrated in vacuo and neutralized with 2M aqueous potassium bicarbonate. The product was extracted into ethyl acetate (3×100 mL). The combined extracts were dried over sodium sulfate, filtered, and evaporated to give 17.0 g (ca. 100%+entrained solvent) ofthe free-amino compound as a white semi-solid: $R_f$=0.12 (10% methanol/dichloromethane).

To a stirred solution of CBZ-glycine (7.32 g, 35.0 mmol) and N-methylmorpholine (4.2 mL, 4.0 g, 38.5 mmol) in tetrahydrofuran (50 mL) at −15° C. was added isobutyl chloroformate (4.8 mL, 5.0 g, 36.8 mmol). After 2 min. a solution of the protected dipeptide (13.9 g, 24.3 mmol) in tetrahydrofuran (50 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M $KHCO_3$(3×100 mL), water, and brine. The resulting solution was dried over sodium sulfate, filtered, and evaporated to give 17.7 g (95%) of the blocked tripeptide as a white solid ($R_f$=0.51, 10% methanol/dichloromethane).

To a suspension of the blocked tripeptide (17.7 g, 23.2 mmol) in ethanol (250 mL) was added water, until the mixture became very turbid (about 100 mL). The resulting mixture was shaken with palladium chloride (4.25 g, 24.0 mmol) under an atmosphere of hydrogen (5 atm) for 18 h. The catalyst was removed by filtration and the filtrate was evaporated to give a white semi-solid. This material was dissolved in water, filtered through 0.45 m nylon syringe filters, and lyophilized to give 10.2 g (ca. 100%) of the desired tripeptide dihydrochloride as a white powder: $[a]_D$− 14.6° (c 2, water); $^1$H NMR (500 MHz, $D_2O$) d 8.81(1H, br s), 8.30(1H, br s), 7.92(1H, br s), 4.37(1H, br s), 3.96(1H, d, J=4.8), 3.58(2H, d, J=8.8), 3.13(2H, br s), 2.74(2H, br s), 1.90–1.20(10H, m); $^{13}$C NMR (125 MHz, $D_2O$) d 175.2, 170.5, 166.9, 157.5, 115.0, 53.7, 52.6, 31.4, 29.2, 27.8, 26.8, 25.0, 22.5, 19.1.

EXAMPLE 9

L-Alanyl-L-Histidyl-L-Lysine

AHK may be obtained as an acetate salt from Bachem Bioscience Inc., Philadephia, Pa. (Catalog No. #1555). Alternatively, AHK may be synthesized as the dihydrochloride salt by the following procedure.

To a stirred solution of $N^\alpha$-BOC-$N^{im}$-CBZ-L-histidine (9.74 g, 25.0 mmol) and N-methylmorpholine (5.8 mL, 5.3 g, 52.5 mmol) in tetrahydrofuran (50 mL) at −15° C. was added isobutyl chloroformate (3.4 mL, 3.6 g, 26.3 mmol). After 2 min. (N-ε-CBZ)-L-lysine benzyl ester hydrochloride (10.2 g, 25.0 mmol) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M $KHCO_3$ (3×100 mL), water, and brine. The resulting solution was dried over sodium sulfate, filtered, and evaporated to give 17.2 g (93%) of the blocked dipeptide as a white semi-solid ($R_f$=0.61, 10% methanol/dichloromethane), which was used in the following transformation without further purification.

A solution of the t-butyloxycarbonyl protected dipeptide (17.2 g, 23.2 mmol) in 35% trifluoroacetic acid/dichloromethane (150 mL) was stirred ½ h at room temperature. The resulting solution was concentrated in vacuo and neutralized with 2M aqueous potassium bicarbonate. The product was extracted into ethyl acetate (3×150 mL). The combined extracts were dried over sodium sulfate, filtered, and evaporated to give 16.8 g (ca. 100%+entrained solvent) of the free-amino compound as a white solid: $R_f$=0.26 (10% methanol/dichloromethane).

To a stirred solution of N-CBZ-L-alanine (6.28 g, 25.0 mmol) and N-methylmorpholine (3.0 mL, 2.8 g, 27.5 mmol) in tetrahydrofuran (50 mL) at −15° C. was added isobutyl chloroformate (3.4 mL, 3.6 g, 26.3 mmol). After 2 min. a solution of the above protected dipeptide (14.9 g, 23.2 mmol) in tetrahydrofuran (50 mL) was added. The reaction mixture was stirred at −15° C. for 1.5 h and then allowed to warm to 0° C. At this time the reaction was quenched by the addition of 2M aqueous potassium bicarbonate. The products were extracted with ethyl acetate (3×150 mL). The combined extracts were washed with 1M citric acid (3×100 mL), water, 2M $KHCO_3$(3× 100 mL), water, and brine. The resulting solution was dried over sodium sulfate, filtered, and evaporated to a syrup, from which the blocked tripeptide was precipitated by dilution with 95% ethanol (300 mL). The resulting material was collected on a filter, washed with 95% ethanol and dried to give a white solid: ($R_f$=0.49, 10% methanol/dichloromethane); mp 151°–153° C.

To a suspension of the blocked tripepride (21.5 g, 21.9 mmol) in ethanol (200 mL) was added water (about 200 mL). The resulting mixture was shaken with palladium chloride (4.25 g, 24.0 mmol) under an atmosphere of hydrogen (5 atm) for 1 h. The resulting mixture, in which the bulk of the material (other than the catalyst) became dissolved, was filtered and the flitrate was concentrated in vacuo to remove volatile organics. The remaining aqueous solution was lyophilized to give 10.88 g of a white solid. This material was dissolved in water, filtered through a 0.2 m nylon membrane, and, again, lyophilized to give 10.50 g (99%) of the desired tripeptide dihydrochloride as a white powder: $[a]_D$−4.43° (c 3, $H_2O$); $^1$H NMR (500 MHz, DMSO-$d_6$) d 8.73 (1H, d, J=7.8), 8.45 (1H, d, J=7.5), 8.09 (1H, s), 7.08 (1H, s), 4.59 (1H, dd, J=5.4, 7.5), 4.12 (1H, m), 3.88 (1H, q, J=6.9), 3.03 (1H, dd, J=15.0, 4.8), 2.96 (1H, dd, J=15.0, 7.7), 2.74 (2H, t, J=7.5), 1.76–1.68 (1H, m), 1.66–1.51 (3H, m), 1.41–1.21 (2H, m), 1.32 (3H, d, J=7.0); $^{13}$C NMR (125 MHz, DMSO-$d_6$) d 174.0, 169.9, 169.5, 134.2, 130.5, 117.8, 52.6, 52.5, 48.0, 38.4, 30.3, 28.2, 26.5, 22.4, 17.2.

EXAMPLE 10

Synthesis of Peptide-Copper Complexes at Various Molar Ratios of Peptide to Copper

A. Peptide-Copper Complex at a 2:1 Molar Ratio

A solution of AHK was prepared by dissolving 2.6954 (0.0065 mole) of the AHK acetate (Bachem Bioscience Inc.) in approximately 10 ml of distilled water. The initial pH of this AHK solution was 6.71. Separately, a solution of copper(II) chloride was prepared by dissolving 0.4479 gm (0.0033 mole) of anhydrous copper(II) chloride in approximately 2.0 ml of distilled water. The copper(II) chloride solution was slowly added to the rapidly stirring AHK solution and the pH was constantly monitored with a pH meter. After all the copper(II) chloride solution was added, the combined solution pH was 3.83. The pH was then adjusted to 7.16 by the slow addition of a solution of 0.5M NaOH, and the final volume was adjusted to 20.0 ml by addition of distilled water. This procedure yielded an aqueous solution containing AHK:Cu at a molar ratio of peptide to copper of 2:1, and at a concentration of 10 mg/ml. The solution was a dark blue-purple and had a characteristic absorption maximum at 563 to 580 nm.

B. peptide-Copper Complex at a 2:1 Molar Ratio

AHK was prepared as the dihydrochloride salt as described in Example 9. A solution of AHK was prepared by dissolving 0.6388 gm (0.00146 mole) of L-alanyl-L-histidyl-L-lysine hydrochloride in approximately 5 ml of distilled water. The initial pH of this AHK solution was 2.45. Separately, a solution of copper(II) chloride was prepared by dissolving 0.0967 gm (0.0007 mole) of anhydrous copper(II) chloride in approximately 1.0 ml of distilled water. The copper(II) chloride solution was slowly added to the rapidly stirring AHK solution and the pH was constantly monitored with a pH meter. After all the copper(II) chloride solution was added, the combined solution pH was 2.36. The pH was then adjusted to 7.05 by the slow addition of a solution of 0.5M NaOH, and the final volume was adjusted to 20.0 ml by addition of distilled water. This procedure yielded an aqueous solution containing AHK:Cu at a molar ratio of peptide to copper of 2:1, and at a concentration of 10 mg/ml. The solution was a dark blue-purple and had a characteristic absorption maximum at 563 to 580 nm.

C. Peptide-Copper Complex at a 1.1:1 Molar Ratio

AHK was prepared as the dihydrochloride salt as described in Example 9. A solution of AHK was prepared by dissolving 1.6144 gm (0.0037 mole) of L-alanyl-L-histidyl-L-lysine hydrochloride in approximately 10 ml of distilled water. The initial pH of this AHK solution was 2.70. Separately, a solution of copper(II) chloride was prepared by dissolving 0.4267 gm (0.0032 mole) of anhydrous copper(II) chloride in approximately 2.0 ml of distilled water. The copper(II) chloride solution was slowly added to the rapidly stirring AHK solution and the pH was constantly monitored with a pH meter. After all the copper(II) chloride solution was added, the combined solution pH was 2.14. The pH was then adjusted to 6.89 by the slow addition of a solution of 0.5M NaOH, and the final volume was adjusted to 20.0 ml by addition of distilled water. This procedure yielded an aqueous solution containing AHK:Cu at a molar ratio of peptide to copper of 1.1:1, and at a concentration of 7.5 mg/ml. The solution was a dark blue-purple and had a characteristic absorption maximum at 593 nm, and a broad peak at 586 to 607 nm.

D. Peptide-Copper Complex at a 1:1 Molar Ratio

A solution of AHK was prepared by dissolving 1.3007 gm (0.0007 mole) of AHK acetate (Bathem Biosceince Inc.) in approximately 5 ml of distilled water. The initial pH of this AHK solution was 6.95. Separately, a solution of copper(II) chloride was prepared by dissolving 0.0966 gm (0.0007 mole) of anhydrous copper(II) chloride in approximately 2.0 ml of distilled water. The copper(II) chloride solution was slowly added to the rapidly stirring AHK solution and the pH was constantly monitored with a pH meter. After all the copper(II) chloride solution was added, the combined solution pH was 2.91. The pH was then adjusted to 7.08 by the slow addition of a solution of 0.5M NaOH, and the final volume was adjusted to 15.0 ml by addition of distilled water. This procedure yielded an aqueous solution containing AHK:Cu at a molar ratio of peptide to copper of 1:1, and at a concentration of 10 mg/ml. The solution was a dark blue-purple and had a characteristic absorption maximum at 595 nm, and a broad peak at 584 to 612 nm.

EXAMPLE 11

Stimulation of Hair Growth by Representative Copper-Peptide Complexes

The following example illustrates the stimulation of hair growth in warm-blooded animals after intradermal injection of representative peptide-copper complexes of this invention.

In this experiment, the backs of C3H mice (60 days old, telogen hair growth phase) were closely clipped on day 1 using an electric clipper. A sterile saline solution containing the indicated peptide-copper complex was then injected intradermally (i.e., infiltrated under the skin) at two locations within the clipped areas of the mice. Injection at two locations provided two test locations within the clipped area of each mouse. Each injection (0.1 ml) contained between 0.36 to 0.55 mg of the peptide-copper complex within the sterile saline solution. A group of saline injected mice (0.1 ml) served as controls. Following injection of the peptide-copper complexes, indications of hair growth were seen within 10 days. The first visual signs were a darkening of the skin in a circular region surrounding the injection site. The size of this region is generally dose dependent, increasing with an increase in dose. The 0.1 ml injections used in this experiment produced a circle of hair growth measuring approximately 0.5 cm² to 5.0 cm² in diameter. Active hair growth occurred between 14–20 days following injection, with a maximum effect seen by day 29. Both the number of mice growing hair at the injection site and the diameter of the hair growth region were determined at day 21. A positive response was expressed as the number of mice exhibiting hair growth at the injection sites compared to the total number of mice injected in the study. The results of this experiment are presented in Table 4 below (the day of onset is the day at which hair follicle pigmentation was first observed):

TABLE 4

Stimulation of Hair Growth by Peptide-Copper Complexes

| Peptide-Copper Complex | Molar Ratio (peptide to copper) | Dose (mg/injection) | Number of Animals Growing Hair | Day of Onset |
|---|---|---|---|---|
| GHKF:Cu | 2:1 | 0.36 mg | 4/5 | 10 |
| PHKF:Cu | 2:1 | 0.43 mg | 5/5 | 10 |
| (N-methyl) GHKVFV:Cu | 2:1 | 0.55 mg | 5/5 | 10 |
| GHKVF:Cu | 2:1 | 0.43 mg | 5/5 | 10 |
| SALINE | — | — | 0/5 | NA |

EXAMPLE 12

Stimulation of Hair Growth by Representative Peptide-Copper Complexes

The following example illustrates the stimulation of hair growth in warm-blooded animals after intradermal injection of representative peptide-copper complexes of this invention.

As in Example 11 above, the backs of C3H mice (60 days old, telogen hair growth phase) were closely clipped on day 1 using an electric clipper. A sterile saline solution containing the indicated peptide-copper complex was then injected intradermally (i.e., infiltrated under the skin) at two locations within the clipped areas of the mice. Injection at two locations provided two test locations within the clipped area of each mouse. Each injection (0.1 ml) contained between 0.75 to 1.5 mg of the peptide-copper complex within the sterile saline solution. A group of saline injected mice (0.1 ml) served as controls. Following injection of the peptide-copper complexes, indications of hair growth were seen within 10 days. The first visual signs were a darkening of the skin in a circular region surrounding the injection site. The size of this region is generally dose dependent, increasing with an increase in dose. The 0.1 ml injections used in this experiment produced a circle of hair growth measuring approximately 0.5 cm² to 5 cm² in diameter. Active hair growth occurred between 14–20 days following injection, with a maximum effect seen by day 29. Both the number of mice growing hair at the injection site and the diameter of the hair growth region were determined at day 21. A positive response was expressed as the number of mice exhibiting hair growth at the injection sites compared to the total number of mice injected in the study. The results of this experiment are presented in Table 5.

TABLE 5

Stimulation of Hair Growth by Peptide-Copper Complexes

| Peptide-Copper Complex | Molar Ratio (peptide to copper) | Dose (mg/injection) | Number of Animals Growing Hair | Area of Hair Growth |
|---|---|---|---|---|
| PHK:Cu | 2:1 | 1.00 | 2/5 | >1 cm diameter |
| GHL:Cu | 2:1 | 1.50 | 3/4 | >1 cm diameter |
| GHE:Cu | 2:1 | 1.50 | 2/4 | >1 cm diameter |
| PHA:Cu | 2:1 | 1.50 | 1/4 | <1 cm diameter |
| PHF:Cu | 2:1 | 0.75 | 4/4 | >1 cm diameter |
| PBL:Cu | 2:1 | 1.50 | 2/4 | <1 cm diameter |
| AHK:Cu | 2:1 | 0.75 | 1/4 | <1 cm diameter |
| AHK:Cu | 2:1 | 1.50 | 4/4 | >1 cm diameter |
| VHK:CU | 2:1 | 0.75 | 3/4 | <1 cm diameter |
| VHK:CU | 2:1 | 1.50 | 4/4 | >1 cm diameter |

EXAMPLE 13

Stimulation of Hair Growth by Peptide-Copper Complexes Containing D-Amino Acids

This example illustrates the stimulation of hair growth in warm-blooded animals by intradermal injection of AHK:Cu (1.1:1) utilizing a D-amino acids inplace of the naturally occurring L-amino acid.

In this experiment, the backs of C3H mice (60 days old, telogen hair growth phase) were closely clipped on day 1 using an electric clipper. A sterile saline solution containing AHK:Cu (1.1:1), or AHK:Cu (1.1:1) containing a D-amino acid, was then injected intradermally (i.e., infiltrated under the skin) at two locations within the clipped areas of the mice. Injection at two locations provided two test locations within the clipped area of each mouse. Each injection (0.1 ml) contained either 1.2 or 1.8 μmoles per injection of peptide-copper complex in the sterile saline solution. A group of saline injected mice (0.1 ml) served as controls. Following injection of peptide copper complex, indications of hair growth were seen within 10 days. The first visual signs were a darkening of the skin in a circular region surrounding the injection site. The size of this region is generally dose dependent, increasing with an increase in dose. The 0.1 ml injections used in this experiment produced a circle of hair growth measuring approximately 0.5 $cm^2$ to 5 $cm^2$ in diameter. Active hair growth occurred between 14–20 days following injection, with a maximum effect seen by day 29.

The degree of hair growth was determined by measuring the total area of hair growth at the two injection sites. The data from this experiment is presented in Table 6.

TABLE 6

Stimulation of Hair Growth by Peptide-Copper Complexes Containing D-Amino Acids

| Peptide-Copper Complex | Molar Ratio (peptide to copper) | Dose (μmoles per injection) | Area of Hair Growth |
|---|---|---|---|
| AHK:Cu | 1.1:1 | 1.2 | 3.07 ± 0.76 |
| AHK:Cu | 1.1:1 | 1.8 | 3.24 ± 1.17 |
| AH-(D)K:Cu | 1.1:1 | 1.2 | 3.30 ± 0.30 |
| AH-(D)K:Cu | 1.1:1 | 1.8 | 3.94 ± 0.35 |
| (D)A-HK:Cu | 1.1:1 | 1.2 | 1.88 ± 0.57 |
| (D)A-HK:Cu | 1.1:1 | 1.8 | 2.68 ± 0.49 |

The table above illustrates that the substitution of D-amino acids for a corresponding L-amino acids dose not effect the hair growth activity of the peptide copper complexes.

EXAMPLE 14

Stimulation of Hair Growth by Topical Application of a Peptide-Copper Complex

This example illustrates the stimulation of hair growth in warm-blooded animals by topical application of a peptide-copper complex. In this experiment, telogen cycle female C3H mice (60–65 days old) were prepared by clipping their posterior dorsal region (i.e., day 1). Topical application of peptide-copper complexes was performed twice per day (Monday–Friday) using a cotton-tipped applicator which delivered approximately 0.1 ml per treatment. The topical formulation used in this experiment contained the following components:

| | |
|---|---|
| Peptide copper Complex | 0.1–0.5% (w/w) |
| Sterde Water | 16.9–16.5% (w/w) |
| Propylene Glycol | 50.0% (w/w) |
| Ethanol | 30.0% (w/w) |
| Nonoxynol-9 | 3.0% (w/w) |

Topical application of the above formulation continued until the onset of follicle pigmentation, which proceeds the emergence of the hair shall. Measurement of the degree of response was performed using digital image analysis at weekly intervals, beginning at day 14. Data was expressed as the percent treatment area response using the following equation:

% treatment area=(growth area/treatment area)×100

For comparison purposes to illustrate the effect of hydrophobic amino acid residues on hair growth after topical application, AHK:Cu was compared to AHF:Cu. In this experiment, topical formulations containing AHK:Cu (1.1:1) and AHF:Cu (1.1:1) were prepared at a concentration of 0.5% and 0.1% (w/w) as indicated above. Hair growth response (i.e., "Percent Treatment Area") was determined at day 20, day 27 and at day 34. The results of this experiment are presented in Table 7.

TABLE 7

| Peptide-Copper Complex | Molar Ratio (peptide to copper) | Concentration (% w/w) | Day | Percent Treatment Area |
|---|---|---|---|---|
| AHK:Cu | 1.1:1 | 0.1% | 20 | 1.29 ± 1.29 |
| AHK:Cu | 1.1:1 | 0.1% | 27 | 23.07 ± 18.84 |
| AHK:Cu | 1.1:1 | 0.1% | 34 | 90.14 ± 2.96 |
| AHK:Cu | 1.1:1 | 0.5% | 20 | 75.87 ± 7.64 |
| AHK:Cu | 1.1:1 | 0.5% | 27 | 100 |
| AHK:Cu | 1.1:1 | 0.5% | 34 | 100 |
| AHF:Cu | 1.1:1 | 0.1% | 20 | 0.00 |
| AHF:Cu | 1.1:1 | 0.1% | 27 | 0.00 |
| AHF:Cu | 1.1:1 | 0.1% | 34 | 12.91 ± 12.91 |
| AHF:Cu | 1.1:1 | 0.5% | 20 | 55.05 ± 17.44 |
| AHF:Cu | 1.1:1 | 0.5% | 27 | 100 |
| AHF:Cu | 1.1:1 | 0.5% | 34 | 100 |

The data presented in Table 7 illustrates that peptide-copper complexes containing hydrophilic residues (i.e., lysine amino acid of AHK:Cu) are more active in stimulating hair growth than similar peptides containing hydrophobic amino acid residues (i.e., the phenylalanine amino acid of AHF:Cu) following administration by topical administration. This is in contrast to administration by injection where peptide-copper complexes containing hydrophilic residues are less active than than similar peptides containing hydrophobic amino acid residues.

EXAMPLE 15

Stimulation of Hair Growth by Intraperitoneal Injection of Peptide-Copper Complexes The following experiment illustrates the maintenance of hair follicle viability (i.e., growth) by intraperitoneal (systemic) injection of the peptide-copper complex GHKVFV:Cu during treatment with the chemotherapeutic agent cytosine arabinoside (Ara-C).

In this experiment, Sprague-Dawley rat pups (age 8 days) were maintained in 4 litters (n=10/litter) for the duration of this study. On day 0, litters received intraperitoneal (IP) injections of GHKVFV:Cu (2:1) in a sterile saline solution, or a saline control (1 injection per animal, 0.1 ml per injection). On day 1, all animals began a series of 7 consecutive daily IP injections with Ara-C (50 mg/kg). On day 8, all animals were evaluated for the extent of hairloss (alopecia) using the following rating scale:

| Grade | Degree of Alopecia |
|---|---|
| 0 | Normal (no loss of hair) |
| 1 | Slight thinning |
| 2 | Moderate thinning |
| 3 | Sparse hair cover |
| 4 | Total loss of hair |

Ara-C injections caused significant hair loss by day 5–6 in most animals. In order to evaluate the effect of GHKVFV:Cu, the degree of hairloss was evaluated daily. Injection of GHKVFV:Cu at a dosage of 50 mg/kg caused a mild retention of hair on the body of the test animals. This was primarily seen on the head, with sparse remaining hair on the body. This was in contrast to the saline control (+Ara-C) group which showed total hair loss. Table 8 presents the results of this experiment as evaluated on day 8 using the previously described rating scale, with the "Degree of Alopecia" being expressed as the average response for all animals.

TABLE 8

| Peptide-Copper Complex | Dose per injection (mg) | Animal Dosage (mg/kg) | n = | Degree of Alopecia (mean) |
|---|---|---|---|---|
| Saline Only | — | 0.0 | 10 | 0.0 |
| Saline + Ara-C | — | 0.0 | 10 | 4.0 |
| GHKVFV:Cu + Ara-C | 1.00 | 50 | 10 | 3.0 |

The observation of retained hair was confirmed histologically on day 8. Of the animals receiving 50 mg/kg of GHKVFV:Cu, approximately 30–40% of dorsal hair was found to be in anagen, compared to 5–10% for animals receiving saline+Ara-C alone. Saline control animals not receiving Ara-C had 100% anagen follicles.

EXAMPLE 16

Stimulation of Hair Growth by Intradermal Injection of Peptide-Copper Complexes

The following experiment illustrates the localized maintenance of hair follicle viability (i.e., growth) by intradermal (local) injection of the peptide-copper complex AHK:Cu during treatment with the chemotherapeutic agent cytosine arabinoside (Ara-C).

In this experiment, Sprague-Dawley rat pups (age 8 days) were maintained in 5 litters (n=10–11/litter) for the duration of this study. On day 0, litters received intradermal (ID) injections of AHK:Cu (1:1) in a sterile saline solution, or a saline control (1 injection per animal, 0.05 ml per injection). Each litter contained 2 normal control animals where no AHK:Cu or Ara-C was administered (i.e., saline only). On day 1, designated animals began a series of 7 consecutive daily intraperitoneal (IP) injections with Ara-C (25 mg/kg). On day 10, all animals were evaluated for the extent of hairloss (alopecia) at the injection sites using the rating identified in Example 15.

Ara-C injections caused significant hair loss by day 5–6 in most animals. In order to evaluate the stimulatory effect of AHK:Cu, the degree of hairloss was evaluated at the injection site daily. AHK:Cu injection generally caused a retention of hair in a 0.25 cm radius around the injection site, most notably in the 0.1 to 0.5 mg dose groups. Table 9 presents the results as evaluated on day 10 using the previously described rating scale, with the the "Degree of Alopecia" being expressed as the average response seen at the site of injection.

TABLE 9

| Peptide-Copper Complex | Dose per injection (mg) | Animal Dosage (mg/kg) | n = | Degree of Alopecia (mean) |
|---|---|---|---|---|
| Saline Only | — | 0.0 | 8 | 0.00 |
| Saline + Ara-C | --- | 0.0 | 8 | 4.00 |
| AHK:Cu + Ara-C | 0.05 | 3.5 | 8 | 3.25 |
| AHK:Cu + Ara-C | 0.10 | 7.0 | 8 | 2.38 |
| AHK:Cu + Ara-C | 0.25 | 17.5 | 9 | 1.44 |
| AHK:Cu + Ara-C | 0.50 | 35.0 | 9 | 1.11 |

The observation of retained hair within the area of AHK:Cu injection was examined histologically. While normal appearing and functioning anagen hair follicles were seen at the injection site of AHK:Cu, follicles located away from the injection were dystrophic and non-functional (disruption of the integrity of inner and outer root sheaths, and displaced hair shafts). These data confirm the gross observations of normal hair follicle function within the site of AHK:Cu injection, and illustrate the stimulatory effect of AHK-Cu on the hair follicle which maintains the active growth cycle during chemotherapy treatment.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method for stimulating hair-growth on an animal in need thereof, comprising administering topically or by injection to the animal an effective amount of a peptide-copper complex having the structure:

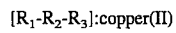

[R$_1$-R$_2$-R$_3$]:copper(II)

wherein R$_1$ is an amino acid or amino acid derivative; R$_2$ is histidine or arginine; and R$_3$ is at least one amino acid or amino acid derivative joined to R$_2$ by a peptide bond, with the proviso that R$_1$ is not glycyl, alanyl, seryl or valyl when R$_2$ is histidyl and R$_3$ is lysine, lysyl-prolyl-valyl-phenylalanyl-valine, lysyl-valyl-phenylalanyl-valine, lysyl-tryptophan, or lysyl-(glycyl)$_{1-2}$-tryptophan, and with the further proviso that R$_1$ is not lysyl when R$_2$ is histidyl and R$_3$ is glycine, glycyl-prolyl-valyl-phenylalanyl-valine, glycyl-valyl-phenylalanyl-valine, glycyltryptophan, or glycyl-(glycyl)$_{1-2}$-tryptophan.

2. The method of claim 1 wherein R$_1$ is an antino acid.

3. The method of claim 1 wherein R$_2$ is histidine.

4. The method of claim 1 wherein R$_2$ is arginine.

5. The method of claim 1 wherein R$_3$ is at least one amino acid.

6. The method of claim 1 wherein R$_3$ is an amino acid.

7. The method of claim 1 wherein administration of the peptide-copper complex is by topical administration.

8. The method of claim 7 wherein R$_1$ is a hydrophilic amino acid.

9. The method of claim 7 wherein R$_3$ is a hydrophilic amino acid.

10. The method of claim 1 wherein the animal has a hair-loss affliction selected from the group consisting of androgenetic alopecia, alopecia areata, female pattern baldness and secondary alopecia.

11. The method of claim 10 wherein the hair-loss affliction is androgenetic alopecia.

12. The method of claim 10 wherein the hair loss affliction is secondary alopecia.

* * * * *

UNITED STATES PATENT AND TRADEMARK OFFICE
CERTIFICATE OF CORRECTION

PATENT NO.    :    5,538,945
DATED         :    July 23, 1996
INVENTOR(S)   :    Alexander J. Pallenberg et al.

It is certified that error appears in the above identified patent and that said Letters Patent is hereby corrected as shown below:

In column 26, line 54, please delete "antino" and insert therefor --amino--.

Signed and Sealed this

Twenty-second Day of October, 1996

Attest:

BRUCE LEHMAN

*Attesting Officer*    *Commissioner of Patents and Trademarks*